(12) United States Patent
Pastor et al.

(10) Patent No.: US 8,388,940 B2
(45) Date of Patent: Mar. 5, 2013

(54) MASCARA COMPOSITIONS

(75) Inventors: Sharon Pastor, Keansbug, NJ (US); Balanda Atis, Newark, NJ (US)

(73) Assignee: L'Oreal, Paris (FR)

( * ) Notice: Subject to any disclaimer, the term of this patent is extended or adjusted under 35 U.S.C. 154(b) by 1092 days.

(21) Appl. No.: 11/373,298

(22) Filed: Mar. 13, 2006

(65) Prior Publication Data

US 2007/0212315 A1    Sep. 13, 2007

(51) Int. Cl.
*A61K 8/81* (2006.01)
(52) U.S. Cl. .................................................. 424/70.7
(58) Field of Classification Search .................. None
See application file for complete search history.

(56) References Cited

U.S. PATENT DOCUMENTS

| | | | |
|---|---|---|---|
| 6,166,093 A | 12/2000 | Mougin et al. | |
| 6,500,439 B1 | 12/2002 | Morita et al. | |
| 2002/0114773 A1 | 8/2002 | Kanji et al. | |
| 2002/0168335 A1 | 11/2002 | Collin | |
| 2003/0068348 A1 | 4/2003 | Ferrari et al. | |
| 2003/0072730 A1 | 4/2003 | Tournilhac | |
| 2003/0170188 A1 | 9/2003 | Ferrari et al. | |
| 2004/0028636 A1 | 2/2004 | Collin | |
| 2004/0126401 A1 | 7/2004 | Collin | |
| 2004/0180032 A1* | 9/2004 | Manelski et al. | 424/70.121 |
| 2005/0009989 A1 | 1/2005 | Liew et al. | |
| 2005/0106193 A1 | 5/2005 | Zofchak et al. | |
| 2005/0180936 A1 | 8/2005 | Pays | |
| 2006/0127344 A1* | 6/2006 | Zofchak et al. | 424/70.31 |

FOREIGN PATENT DOCUMENTS

| | | |
|---|---|---|
| JP | 07-196450 | 8/1995 |
| JP | 07-267827 | 10/1995 |
| JP | 9-012425 | 1/1997 |
| JP | 2002-537314 | 11/2002 |
| JP | 2002-370919 | 12/2002 |
| JP | 2003-012462 | 1/2003 |
| JP | 2003-055155 | 2/2003 |
| JP | 2003-521489 | 7/2003 |
| JP | 2004/59564 | 2/2004 |
| JP | 2004-515511 | 5/2004 |
| JP | 2004-515514 | 5/2004 |
| JP | 2004-520457 | 7/2004 |
| JP | 2004-525101 | 8/2004 |
| JP | 2005-029575 | 2/2005 |
| JP | 2005-225867 | 8/2005 |
| WO | WO 98/55078 | 12/1998 |
| WO | WO 00/49997 | 8/2000 |
| WO | WO 01/54660 | 8/2001 |
| WO | WO 02/47619 | 6/2002 |
| WO | WO 2004/066918 A2 | 8/2004 |
| WO | WO 2004/087078 A1 | 10/2004 |
| WO | WO 2006/065878 | 6/2006 |
| WO | WO 2007/024978 | 3/2007 |

OTHER PUBLICATIONS

U.S. Appl. No. 11/585,225, filed Oct. 24, 2006, Atis.
Office Action issued Sep. 21, 2010, in Japanese Patent Application 2007-062879, filed Mar. 13, 2007 (English Translation).
Office Action issued May 8, 2012 in Japanese Patent Application No. 2007-62879 (with English translation).
European Search Report issued Nov. 5, 2012, in European Patent Application No. 07005146.1.
Office Action issued Nov. 16, 2012, in European Patent Application No. 07005146.1.

* cited by examiner

*Primary Examiner* — Brian Gulledge
(74) *Attorney, Agent, or Firm* — Oblon, Spivak, McClelland, Maier & Neustadt, L.L.P.

(57) ABSTRACT

The invention relates to compositions for eyelashes such as mascaras, topcoats and basecoats containing (a) at least one fatty alkoxylated dimeric compound; and (b) at least one polymeric compound selected from the group consisting of a polyorganosiloxane-containing polymer, a non-silicone polyamide copolymer, a hydrocarbon resin, a styrene-containing copolymer, and mixtures thereof.

9 Claims, No Drawings

MASCARA COMPOSITIONS

FIELD OF THE INVENTION

The present invention generally relates to compositions for eyelashes such as mascaras, topcoats and basecoats comprising at least one fatty alkoxylated dimeric compound and a polymeric compound selected from the group consisting of a polyorganosiloxane-containing polymer, a non-silicone polyamide copolymer, a hydrocarbon resin, a styrene-containing copolymer, and mixtures thereof. Such compositions possess improved properties and characteristics such as, for example, increasing eyelash length and/or volume or increasing transfer-resistance, waterproofing and/or long-wear properties.

DISCUSSION OF THE BACKGROUND

Many mascaras and other cosmetic compositions have been developed for longer wear and transfer resistance properties. This is typically accomplished by the use of ingredients that form a film after application. Such compositions generally contain volatile solvents, which evaporate on contact with the skin or eyelashes, leaving behind a layer comprising waxes and/or resins, pigments, fillers, and actives. However, these compositions can be uncomfortable for the wearer as the composition remains on the skin or eyelashes as a brittle or non-flexible film. Such compositions may not be pliable or soft, and they may not be comfortable to wear. There may also be a tendency for such compositions to flake off because of poor adherence to the skin or eyelashes. Furthermore, such compositions have a tendency to be tacky, resulting in poor application, spreadability and wear characteristics.

Thus, there remains a need for improved long-wearing cosmetic compositions which transfer little or not at all, i.e., "transfer-free" or transfer resistant compositions which also possess good cosmetic properties such as pliability and comfort. For example, a composition that is transfer resistant may deposit a film onto a keratinous substance that may not transfer when the keratinous substance comes into contact with, for example, skin, clothes, a cup, paper, cigarette, or a handkerchief.

Accordingly, one aspect of the present invention is a care and/or makeup and/or treatment composition for eyelashes which is able to address or overcome at least one of the aforementioned problems with the prior art compositions.

SUMMARY OF THE INVENTION

The present invention relates to compositions for eyelashes such as mascaras, topcoats and basecoats comprising (a) at least one fatty alkoxylated dimeric compound; and (b) at least one polymeric compound selected from the group consisting of a polyorganosiloxane-containing polymer, a non-silicone polyamide copolymer, a hydrocarbon resin, a styrene-containing copolymer, and mixtures thereof.

The present invention also relates to compositions for eyelashes such as mascaras, topcoats and basecoats comprising (a) at least one fatty alkoxylated dimeric compound; (b) at least one hydrocarbon resin; and (c) at least one styrene-containing copolymer.

The present invention also relates to compositions for eyelashes such as mascaras, topcoats and basecoats comprising (a) at least one fatty alkoxylated dimeric compound; (b) at least one polyorganosiloxane-containing polymer; and (c) at least one non-silicone polyamide copolymer.

The present invention also relates to methods of improving performance properties of compositions for eyelashes such as mascaras, topcoats and basecoats such as, for example, transfer-resistance, long-wear and/or waterproofing, comprising combining in a composition (a) at least one fatty alkoxylated dimeric compound; and (b) at least one polymeric compound selected from the group consisting of a polyorganosiloxane-containing polymer, a non-silicone polyamide copolymer, a hydrocarbon resin, a styrene-containing copolymer, and mixtures thereof.

The present invention also relates to methods of increasing eyelash volume and/or length comprising applying to eyelashes an eyelash volume- and/or length-increasing effective amount of a composition comprising (a) at least one fatty alkoxylated dimeric compound; and (b) at least one polymeric compound selected from the group consisting of a polyorganosiloxane-containing polymer, a non-siliconepolyamide copolymer, a hydrocarbon resin, a styrene-containing copolymer, and mixtures thereof.

The present invention further relates to methods of making-up eyelashes comprising applying an eyelash making-up effective amount of a composition comprising (a) at least one fatty alkoxylated dimeric compound; and (b) at least one polymeric compound selected from the group consisting of a polyorganosiloxane-containing polymer, a non-siliconepolyamide copolymer, a hydrocarbon resin, a styrene-containing copolymer, and mixtures thereof, to eyelashes in need of such making-up.

The present invention also relates to methods of treating or caring for eyelashes by applying compositions of the present invention to the eyelashes in an amount sufficient to treat and/or care for the eyelashes.

The present invention further relates to methods of enhancing the appearance of eyelashes by applying compositions of the present invention to the eyelashes in an amount sufficient to enhance the appearance of the eyelashes.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a modified "kiss" test. The modified "kiss" test may involve application of the composition to human eyelashes followed by "kissing" or rubbing a material with the eyelashes, for example, a sheet of paper, after expiration of a certain amount of time following application, such as 2 minutes after application. Similarly, transfer resistance of a composition may be evaluated by the amount of product transferred from a wearer to any other substrate, such as transfer from the eyelashes of an individual to clothing after the expiration of a certain amount of time following application. The amount of composition transferred to the substrate (e.g., clothing or paper) may then be evaluated and compared. For example, a composition may be transfer resistant if a majority of the product is left on the eyelashes. Further, the amount transferred may be compared with that transferred by other compositions, such as commercially available compositions.

"Long wear" compositions as used herein, refers to compositions where at least one property chosen from consistency, texture, and color remains the same as at the time of application, as viewed by the naked eye, after an extended period of time, such as, for example, 1 hour, 2 hours, and further such as 8 hours. Long wear properties may be evaluated by any method known in the art for evaluating such properties. For example, long wear may be evaluated by a test involving the application of a composition to eyelashes and evaluating the consistency, texture and color of the composition after an extended period of time. For example, the consistency, texture and color of a mascara composition may be evaluated immediately following application and these characteristics may then be re-evaluated and compared after an individual has worn the mascara composition for a certain amount of time. Further, these characteristics may be evaluated with respect to other compositions, such as commercially available compositions.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes.

"Tackiness" as used herein refers to measuring the maximum tensile force, $F_{max}$, required while separating two surfaces. Depending on the application envisaged and the formulation being designed, the desirable value for $F_{max}$ may vary. In some embodiments, the substantially non-tacky compositions have a $F_{max}$ of less than about 4 Newton (N), less than about 1 N, less than about 0.5 N, less than about 0.3 N, less than about 0.2 N or less than 0.1 N. One of ordinary skill in the art can determine the $F_{max}$ of the composition by, for example, determining the maximum force of traction, measured with an extensiometer of the LLOYD model LR5K type, needed to detach two surfaces.

For example, two 38 mm² surfaces, A and B, which are solid, rigid, inert, and non-absorbing, are mounted on movable mounts, facing each other. The surfaces may be movable either toward or away from each other, or one may move surface A independently from surface B or vice versa. Prior to insertion into the extensiometer, surface A is coated with the composition to be measured, which may be dissolved in a solvent such as aqueous, hydroalcoholic, hydrocarbon, silicone, and alcoholic solvents in a concentration of from about 10 to about 30%, preferably 20%, the surface A is coated in a thickness of from 1 to 10 mil, preferably 1 mil, and the surface is dried for 24 hours at room temperature, e.g., 22 to 25° C., at a relative humidity of about 50%. Once inserted in the extensiometer, surface A is subjected for 20 seconds to a compression force of 3 N against surface B and then subjected for 30 seconds to tensile force at a rate of 20 mm/minute. The amount of force, $F_{max}$, needed to obtain initial separation is then noted. A mean $F_{max}$ is determined by carrying out the procedure with multiple pairs, preferably at least six pairs, of surface A and surface B.

The cosmetic compositions and methods of the present invention can comprise, consist of, or consist essentially of the essential elements and limitations of the invention described herein, as well as any additional or optional ingredients, components, or limitations described herein or any otherwise useful ingredient found in personal care compositions intended for application to keratin materials.

The composition of the present invention may be in any form suitable for use on eyelashes such as, for example, non-solid anhydrous, oil-free or emulsion compositions (for example, water-in-oil emulsion, oil-in-water emulsion, multiple emulsion (W/O/W or O/W/O), nanoemulsions, etc.). The compositions of the present invention can be mascaras. Generally speaking, mascaras contain colorants such as pigments. Additionally, the compositions of the present invention can be clear or transparent: that is, they can contain little or no colorants. The compositions of the present invention, particularly those with little or no colorants, can be used as a basecoat and/or topcoat for application beneath and/or onto other products applied to eyelashes.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion. The stability is further tested by repeating the 8-week test at 40° C., 37° C., 45° C., 50° C. and/or under freeze-thaw conditions. A composition is considered to lack stability if in any of these tests an abnormality that impedes functioning of the composition is observed. The skilled artisan will readily recognize an abnormality that impedes functioning of a composition based on the intended application.

Fatty alkoxylated dimeric compound

According to the present invention, compositions comprising at least one fatty alkoxylated dimeric compound are provided. Suitable fatty alkoxylated dimeric compounds include those disclosed in U.S. patent application publication no. U.S. 2005/0106193, published May 19, 2005, the entire contents of which are hereby incorporated by reference in its entirety.

More specifically, suitable fatty alkoxylated dimeric compounds include compounds of the formula (I):

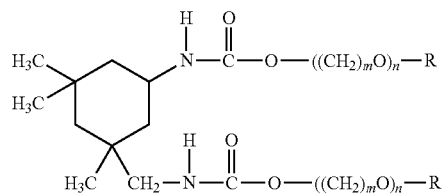

where n is a whole number between about 50 and about 150, preferably between about 70 and about 120, and most preferably between about 75 and 100, including all ranges and subranges therebetween; m is a whole number between 1 and 5, preferably 2 and/or 3 (ethoxylation and/or propoxylation), and most preferably 2 (ethoxylation); and R represents a $C_{12}$-$C_{24}$ alkyl or alkenyl fatty portion, preferably a $C_{14}$-$C_{22}$ fatty portion, and most preferably a $C_{16}$-$C_{18}$ fatty portion.

Preferred fatty alkoxylated dimeric compounds are compounds comprising between about 75 and about 100 ethoxylated units and a $C_{16}$-$C_{18}$ fatty portion. Particularly preferred examples of such compounds are compounds having 75 or 100 mole (or units) of ethoxylation marketed under the tradenames Dermothix 75 and Dermothix 100, respectively.

Preferably, the fatty alkoxylated dimeric compound is present in an amount ranging from about 0.5% to about 40% by weight of the total weight of the composition, more preferably from about 1% to about 30% of the total weight of the composition, more preferably from about 3% to about 20% of the total weight of the composition, and most preferably from about 5% to about 15%, including all ranges and subranges therebetween.

Polymeric Compound

According to the present invention, compositions comprising at least one polymeric compound selected from the group consisting of a polyorganosiloxane-containing polymer, a non-silicone polyamide copolymer, a styrene-containing copolymer, a hydrocarbon resin, and mixtures thereof are provided.

Polyorganosiloxane-containing polymers can generally be described as polymers chosen from homopolymers and copolymers, preferably, with a weight-average molecular mass ranging from about 500 to about $2.5 \times 10^6$ or more, comprising at least one moiety comprising: at least one polyorganosiloxane group comprising, preferably, from 1 to about 10,000 organosiloxane units in the chain of the moiety or in the form of a graft, and at least two groups capable of establishing hydrogen interactions. Examples of suitable polyorganosiloxane-containing polymers can be found in U.S. patent application Ser. No. 11/254,919, filed Oct. 21, 2005, the entire contents of which is hereby incorporated by reference.

More specifically, preferred polyorganosiloxane-containing polymers comprise at least one moiety chosen from formulae (III) and (IV):

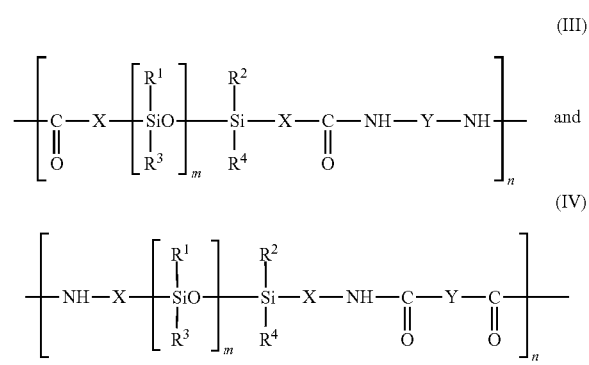

in which:
1) $R^1$, $R^2$, $R^3$ and $R^4$, which may be identical or different, are chosen from:
   linear, branched and cyclic, saturated and unsaturated, $C_1$ to $C_{40}$ hydrocarbon-based groups, optionally comprising in the chain at least one atom chosen from oxygen, sulphur and nitrogen, and also optionally being partially or totally substituted with at least one fluorine atom,
   $C_6$ to $C_{10}$ aryl groups, optionally substituted with at least one $C_1$ to $C_4$ alkyl group,
   polyorganosiloxane chains optionally comprising at least one atom chosen from oxygen, sulphur and nitrogen;

2) the groups X, which may be identical or different, are chosen from linear and branched $C_1$ to $C_{30}$ alkylenediyl groups, optionally comprising in the chain at least one atom chosen from oxygen and nitrogen;
3) Y is chosen from saturated and unsaturated, $C_1$ to $C_{50}$ linear and branched divalent alkylene, arylene, cycloalkylene, alkylarylene and arylalkylene groups, optionally comprising at least one atom chosen from oxygen, sulphur and nitrogen, and optionally substituted by one of the following atoms and groups of atoms:
   fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or
4) Y represents a group corresponding to the formula:

in which
   T is chosen from linear and branched, saturated and unsaturated, $C_3$ to $C_{24}$ trivalent and tetravalent hydrocarbon-based groups optionally substituted with a polyorganosiloxane chain, and optionally comprising at least one atom chosen from O, N and S, or T represents a trivalent atom chosen from N, P and Al, and
   $R^5$ is chosen from linear and branched $C_1$ to $C_{50}$ alkyl groups and polyorganosiloxane chains, optionally comprising at least one group chosen from ester, amide, urethane, thiocarbamate, urea, thiourea and sulphonamide groups, which may optionally be linked to another chain of the polymer;
5) n is an integer ranging from 2 to 500, and m is an integer ranging from 1 to 1 000.

Particularly preferred polyorganosiloxane-containing polymers are polysiloxane-polyamide copolymers available from Dow Corning such as, for example, Nylon-611/Dimethicone copolymer.

Non-silicone polyamide copolymers include but are not limited to those known in the trade as Uniclear or Sylvaclear. These non silicone polyamides have different terminal end groups, such as ester terminated, known as Uniclear 80 or 100, such as amide terminated, known as Sylvaclear A200, and such as polyalkyleneoxy terminated, known as Sylvaclear AF1900 as well as ester terminated polyesteramides. Such non-silicone polyamides are available, for instance, from Arizona Chemical Company, Jacksonville, Fla., and are described in U.S. Pat. Nos. 5,783,657, 6,402,408, 6,268,466, 6,552,160, the entire contents of which are hereby incorporated by reference.

Styrene-containing copolymers result from the copolymerization of at least one styrene monomer with another monomer such as, for example a vinyl, acrylic or methacrylic monomer. This polymer may comprise, for example, a styrene (S) block or an alkylstyrene (AS) block, and a block chosen from ethylene/butylene (EB), ethylene/propylene (EP), butadiene (B), isoprene (I), acrylate (A) and methacrylate (MA) blocks, or a combination of these blocks.

According to preferred embodiments, the styrene-containing polymer is a diblock copolymer (AB) or a triblock copolymer (ABA or ABC). Particularly preferred triblock copolymers include but are not limited to those of the polystyrene/polyisoprene or polystyrene/polybutadiene type, such as those sold or manufactured under the name "Luvitol HSB" by BASF, and those of the polystyrene/copoly(ethylene-propylene) type or alternatively of the polystyrene/copoly(ethylene-butylene) type, such as those sold or manufactured under the brand name "Kraton" by Shell Chemical Co. or Gelled Permethyl 99A by Penreco. Styrene-methacrylate copolymers may also be used.

Specific examples of such polymers include but are not limited to Kraton G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton D-1101 (SBS), Kraton D-1102 (SBS), Kraton D-1107 (SIS), Gelled Permethyl 99A -750, Gelled Permethyl 99A-753-58, Gelled Permethyl 99A-753-59, Versagel 5970 and Versagel 5960 from Penreco, and OS 129880, OS 129881 and OS 84383 from Lubrizol (styrene-methacrylate copolymer).

Suitable diblock or triblock copolymers also include those such as polystyrene-copoly(ethylene/-propylene) or polystyrene-copoly(ethylene/butylene), such as those described in patent applications WO 98/38981 and U.S. 2002/0055562, the entire contents of both of which are hereby incorporated by reference in their entirety.

According to particularly preferred embodiments, compositions of the present invention comprising a polymeric compound, particularly a styrene-containing copolymer, further comprise at least one hydrocarbon-based oil. The term "hydrocarbon-based oil" means an oil essentially formed from, or even consisting of, carbon and hydrogen atoms, and possibly oxygen and nitrogen atoms, and not containing any silicon or fluorine atoms. Such an oil may contain ester, ether, amine or amide groups. Preferably, the hydrocarbon based-oil has a molecular weight of greater than or equal to 400.

The hydrocarbon-based oils with a molecular weight of greater than or equal to 400 used according to the invention are chosen, for example, from alkanes with a melting point of less than 45° C., fatty acid esters, fatty alcohol ethers, and mixtures thereof. Hydrocarbon-based oils with a molecular weight of greater than or equal to 400 that may be mentioned in particular include jojoba oil; fatty acid esters such as isocetyl palmitate and isocetyl stearate; oils of plant origin; fatty alcohol ethers such as diisostearyl ether.

Particularly preferred alkanes with a melting point of less than 45° C. include but are not limited to hydrogenated polyisobutene such as Parleam® oil and liquid petroleum jelly, and mixtures thereof.

According to preferred embodiments, the amount of hydrocarbon oil present may represent from about 25% to about 100% by weight of the oily phase of the composition, preferably from about 25% to about 80% by weight, and most preferably from about 30% to about 70% by weight of the oily phase, including ranges and subranges therebetween.

Examples of commercial products containing both a styrene-containing copolymer and a hydrocarbon-based oil include at least some of the Versagel products available from Penreco such as, for example, Versagel®R and Versagel®RE.

Suitable hydrocarbon resins include but are not limited to aliphatic hydrocarbon resins, hydrogenated aliphatic hydrocarbon resins, aliphatic/aromatic hydrocarbon resins, hydrogenated aliphatic aromatic hydrocarbon resins, cycloaliphatic hydrocarbon resins, hydrogenated cycloaliphatic resins, cycloaliphatic/aromatic hydrocarbon resins, hydrogenated cycloaliphatic/aromatic hydrocarbon resins, aromatic hydrocarbon resins, hydrogenated aromatic hydrocarbon resins, polyterpene resins, terpene-phenol resins, rosins, rosin esters, resins grafted with an unsaturated acid or anhydride, and mixtures of any two or more thereof.

When referring to hydrogenated resins, hydrogenated includes resins that are at least partially hydrogenated and substantially hydrogenated.

Examples of suitable hydrocarbon resins include but are note limited to ESCOREZ™1310 and EMPR™118 available from ExxonMobil Chemical Company, Houston, Tex., PICCOTAC™1020, 1020E, and 9095 available from Eastman Chemical Company, Kingsport, Tenn., WINGTACK™10, 86, PLUS, and 95 available from Goodyear Chemical Company, and QUINTONE™ K100, R100, and M100 available from Nippon Zeon of Japan.

Other suitable hydrocarbon resins are disclosed in U.S. patent application publication No. 2004/0092648, published May 13, 2004, the entire contents of which is hereby incorporated by reference.

Preferably, the polymeric compound is present in an amount ranging from about 0.5% to about 40% by weight of the total weight of the composition, more preferably from about 1% to about 30% of the total weight of the composition, more preferably from about 3% to about 20% of the total weight of the composition, and most preferably from about 5% to about 15%, including all ranges and subranges therebetween.

Coloring Agents

According to the present invention, the compositions may optionally comprise at least one coloring agent. Suitable coloring agents include but are not limited to pigments, dyes, such as liposoluble dyes, nacreous pigments, and pearling agents. Typically, when the composition contains colorants, it is a mascara composition. Alternatively, when the composition does not contain colorants, it is a clear or transparent composition which can be used as a basecoat (or topcoat) prior to (or after) application of a mascara composition to eyelashes. However, it is possible that topcoats or basecoats could contain colorants, and/or that a mascara composition could contain little or no colorant.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the pigments may be present in the composition in a concentration ranging up to 50% by weight of the total weight of the composition, such as from 0.5% to 40%, and further such as from 2% to 30%. In the case of certain products, the pigments, including nacreous pigments, may, for example, represent up to 50% by weight of the composition.

According to particularly preferred embodiments, the compositions of the present invention are in the form of an emulsion. Suitable emulsion forms include but are not limited to oil-in-water, water-in-oil, oil-in-water-in-oil, water-in-oil-in-water and nanoemulsions (emulsions whose oil globules are of very fine particle size, that is to say that they have a number-average size of less than about 100 nanometers (nm)). Emulsions contain at least one oil phase and at least one aqueous phase. Typically speaking, emulsions contain surfactants or surfactant-like materials which provide stability to the emulsions and inhibit de-phasing of the emulsions.

One particularly preferred embodiment of the present invention is a composition for application to eyelashes which is an emulsion but which is substantially free of TEA-stearate (that is, less than 0.25% of TEA-stearate) or free of TEA Stearate (that is, less than 0.05% TEA-stearate).

Additional Ingredients

The compositions of the present invention can also comprise any additive usually used in the field under consideration. For example, film forming agents, dispersants, antioxidants, essential oils, preserving agents, fragrances, liposoluble polymers that are dispersible in the medium, fillers, neutralizing agents, cosmetic and dermatological active agents such as, for example, emollients, moisturizers, vitamins, anti-wrinkle agents, essential fatty acids, sunscreens, and mixtures thereof can be added. A non-exhaustive listing of such ingredients can be found in U.S. patent application Ser. No. 10/733,467, filed Dec. 12, 2003, the entire contents of which is hereby incorporated by reference. Further examples of suitable additional components can be found in the other references which have been incorporated by reference in this application, including but not limited to the applications from which this application claims priority. Still further examples of such additional ingredients may be found in the International Cosmetic Ingredient Dictionary and Handbook (9$^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present).

Needless to say, the composition of the invention should be cosmetically or dermatologically acceptable, i.e., it should contain a non-toxic physiologically acceptable medium and should be able to be applied to the eyelashes of human beings. For the purposes of the invention, the expression "cosmetically acceptable" means a composition of pleasant appearance, odor, feel and/or taste.

Specific examples of additional ingredients include oils, particularly if the composition is an anhydrous composition or an emulsion. Any oils can be used in accordance with the present invention. The oils can be volatile or non-volatile, silicone-based and/or hydrocarbon-based, etc. Thus, for example, the external oil phase may contain, independently or in combination, volatile silicone oils, non-volatile silicone oils, volatile non-silicone oils and non-volatile non-silicone oils.

In one embodiment, the compositions of the present invention are substantially free of silicone oils (i.e., contain less than about 1% of silicone oil). In another embodiment, the compositions are substantially free of non-silicone oils (i.e., contain less than about 1% of non-silicone oil). In another embodiment, the compositions are substantially free of non-volatile oils (i.e., contain less than about 1% of non-volatile oil). In yet another embodiment, the compositions are substantially free of volatile oils (i.e., contain less than about 1% of volatile oil).

According to one embodiment, the oil phase may contain one or more volatile silicone oils. Examples of such volatile silicone oils include linear or cyclic silicone oils having a viscosity at room temperature less than or equal to 6cSt and having from 2 to 7 silicone atoms, these silicones being optionally substituted with alkyl or alkoxy groups of 1 to 10 carbon atoms. Suitable oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 St) from Dow Corning | 102 | 3 |

Further, a volatile linear silicone oil may be employed in the compositions of the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

The volatility of the solvents/oils can be determined using the evaporation speed as set forth in U.S. Pat. No. 6,338,839.

Examples of other silicone oils that may be used in the invention include non-volatile linear polydimethylsiloxanes (PDMSs), that are liquid at room temperature; polydimethylsiloxanes comprising alkyl, alkoxy or phenyl groups, which are pendent and/or at the end of a silicone chain, these groups each containing from 2 to 24 carbon atoms; phenylsilicones, for instance phenyl trimethicones, phenyl dimethicones, phenyl trimethylsiloxydiphenylsiloxanes, diphenyl dimethicones, diphenyl methyldiphenyl trisiloxanes and 2-phenylethyl trimethylsiloxysilicates.

According to other preferred embodiments, the oil phase may contain one or more non-silicone volatile oils and may be selected from volatile hydrocarbon oils, alcohols, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate and their mixtures. Preferably, the volatile non-silicone oils have a flash point of at least 40° C.

TABLE 2

| Compound | Flash Point (° C.) |
| --- | --- |
| Isododecane | 43 |
| Isohexadecane | 102 |
| Isodecyl Neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

Examples of other non-silicone oils which can be used in the compositions of the present invention include polar oils such as:
  hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;
  synthetic oils or esters of formula $R_5COOR_6$ in which $R_5$ represents a linear or branched higher fatty acid residue containing from 1 to 40 carbon atoms, including and better still from 7 to 19 carbon atoms, and $R_6$ represents a branched hydrocarbon-based chain containing from 1 to 40 carbon atoms, including and better still from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;
  synthetic ethers containing from 10 to 40 carbon atoms; $C_8$ to $C_{26}$ fatty alcohols, for instance oleyl alcohol; and mixtures thereof.

Preferably, the oils, if present, represent from about 5% to about 80% by weight of the total weight of the composition, more preferably from about 10% to about 60% of the total weight of the composition, and most preferably from about 15% to about 50%, including all ranges and subranges therebetween.

Water, when present, preferably represents from about 1% to about 70% by weight of the total weight of the composition, more preferably from about 5% to about 60% of the total weight of the composition, and most preferably from about 10% to about 50%, including all ranges and subranges therebetween.

According to preferred embodiments, methods of improving performance properties of compositions for eyelashes such as mascaras, topcoats and basecoats such as, for example, transfer-resistance, long-wear and/or waterproofing, comprising combining in a composition (a) at least one fatty alkoxylated dimeric compound; and (b) at least one polymeric compound selected from the group consisting of a polyorganosiloxane-containing polymer, a non-silicone polyamide copolymer, a hydrocarbon resin, a styrene-containing copolymer, and mixtures thereof, are provided. The compositions may be applied to eyelashes as needed, preferably once or twice daily, more preferably once daily and then preferably allowed to dry before subjecting to contact such as with clothing or other objects.

According to particularly preferred embodiments, sufficient fatty alkoxylated dimeric compound is combined with sufficient polymeric compound such that the performance properties of the compositions are greater than the performance properties of compositions containing either ingredient individually. Thus, in accordance with such particularly preferred embodiments, the compositions for eyelashes contain a transfer-resistance, long-wear and/or waterproofing enhancing effective amount of the fatty alkoxylated dimeric compound and/or the polymeric compound.

According to other embodiments of the present invention, methods of increasing eyelash volume and/or length comprising applying to eyelashes an eyelash volume- and/or length-increasing effective amount of a composition comprising (a) at least one fatty alkoxylated dimeric compound; and (b) at least one polymeric compound selected from the group consisting of a polyorganosiloxane-containing polymer, a non-silicone-polyamide copolymer, a hydrocarbon resin, a styrene-containing copolymer, and mixtures thereof, are provided. The compositions may be applied to eyelashes as needed, preferably once or twice daily, more preferably once daily and then preferably allowed to dry before subjecting to contact such as with clothing or other objects.

According to yet further embodiments of the present invention, methods of making-up eyelashes comprising applying an eyelash making-up effective amount of a composition comprising (a) at least one fatty alkoxylated dimeric compound; and (b) at least one polymeric compound selected from the group consisting of a polyorganosiloxane-containing polymer, a non-silicone-polyamide copolymer, a hydrocarbon resin, a styrene-containing copolymer, and mixtures thereof, to eyelashes in need of such making-up are provided.

According to preferred embodiments of the present invention, methods of treating or caring for eyelashes by applying compositions of the present invention to the eyelashes in an amount sufficient to treat and/or care for the eyelashes are provided.

According to other preferred embodiments, methods of enhancing the appearance of eyelashes by applying compositions of the present invention to the eyelashes in an amount sufficient to enhance the appearance of the eyelashes are provided.

In accordance with the preceding preferred embodiments, the compositions of the present invention are applied topically to eyelashes in an amount sufficient to treat, care for and/or make up the eyelashes, or to enhance the appearance of eyelashes. The compositions may be applied to eyelashes as needed, preferably once or twice daily, more preferably once daily and then preferably allowed to dry before subjecting to contact such as with clothing or other objects.

The present invention also envisages kits and/or prepackaged materials suitable for consumer use containing one or more compositions according to the description herein (for example, kits containing (1) a mascara; and (2) a basecoat and/or topcoat). The packaging and application device for any subject of the invention may be chosen and manufactured by persons skilled in the art on the basis of their general knowledge, and adapted according to the nature of the composition to be packaged. Indeed, the type of device to be used can be in particular linked to the consistency of the composition, in particular to its viscosity; it can also depend on the nature of the constituents present in the composition, such as the presence of volatile compounds.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLE 1

Mascara (emulsion)

| Seq | Trade Name | INCI Name | Amount |
|---|---|---|---|
| A | Water | Water | 43.50 |
| | Methylparaben | Methylparaben | 0.30 |
| | Magnesium Sulfate | Magnesium Sulfate | 1.00 |
| | Hydrolite-5 | Pentylene Glycol | 2.00 |
| | Phenoxyethanol | Phenoxyethanol | 0.50 |
| | Dermothix 100 | Disteareth-100 IPDI and Steareth-100 | 6.00 |
| B1 | Propylparaben | Propylparaben | 0.20 |
| | Beeswax | Beeswax | 5.00 |
| | Carnauba Wax | Carnauba Wax | 3.00 |
| | Phytowax Olive 15L57 | Hydrogenated Stearyl Olive Esters | 5.20 |
| | DC 2-8179 Gellant | Nylon-611/Dimethicone Copolymer | 2.30 |
| | Uniclear 100 VG | EthyleneDiamine/Stearyl Dimer Dilinoleate Copolymer | 3.25 |
| | Paraffin | Paraffin | 1.75 |
| B2 | Black Iron Oxide | Black Iron Oxide | 8.00 |

EXAMPLE 1-continued

Mascara (emulsion)

| Seq | Trade Name | INCI Name | Amount |
|---|---|---|---|
| B3 | DC245 | Cyclopentasiloxane | 15.00 |
| | Mirasil C-DPDM | Cyclopentasiloxane & Diphenyl Dimethicone | 3.00 |
| | | | 100.00 |

What is claimed is:

1. A mascara comprising:
(a) at least one fatty alkoxylated dimeric compound is of formula (I):

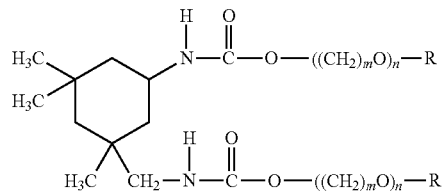

where n is a whole number between 50 and 150; m is a whole number between 1 and 5; and R represents a $C_{12}$-$C_{24}$ alkyl or alkenyl fatty portion; and
(b) at least one nylon-611/dimethicone copolymer.

2. The mascara according to claim 1, wherein the at least one fatty alkoxylated dimeric compound comprises between about 50 and 120 alkoxylated units and a $C_{16}$-$C_{18}$ fatty portion.

3. The mascara according to claim 1, wherein the at least one fatty alkoxylated dimeric compound comprises between about 75 and 100 ethoxylated units and a $C_{16}$-$C_{18}$ fatty portion.

4. The mascara according to claim 1, wherein the mascara is in the form of an emulsion.

5. The mascara according to claim 1, wherein the at least one nylon-611/dimethicone copolymer is present in an amount of 1% to 30% by weight of the total weight of the composition, and the at least one fatty alkoxylated dimeric compound is present in an amount of 1% to 30% by weight of the total weight of the composition.

6. The mascara according to claim 5 where n is a whole number between 75 and 100.

7. The mascara according to claim 1, wherein the at least one nylon-611/dimethicone copolymer is present in an amount of 1% to 30% by weight of the total weight of the composition, and the at least one fatty alkoxylated dimeric compound is present in an amount of 3% to 20% by weight of the total weight of the composition.

8. A method of making-up eyelashes comprising applying the mascara according to claim 1 to eyelashes.

9. A method of increasing eyelash volume or length comprising applying the mascara according to claim 1 to eyelashes.

* * * * *